US007858140B2

(12) United States Patent
Paustian et al.

(10) Patent No.: US 7,858,140 B2
(45) Date of Patent: Dec. 28, 2010

(54) PROCESSES FOR RECOVERY AND SEPARATION OF GRAIN PERICARP FROM ENDOSPERM

(75) Inventors: David Paustian, Vinton, IA (US); Daniel Hammes, Crystal Lake, IL (US); Scott Feller, Dayton, OH (US)

(73) Assignee: Corn Value Products, Kenosha, WI (US)

( * ) Notice: Subject to any disclaimer, the term of this patent is extended or adjusted under 35 U.S.C. 154(b) by 927 days.

(21) Appl. No.: 11/653,562

(22) Filed: Jan. 16, 2007

(65) Prior Publication Data

US 2007/0184159 A1 Aug. 9, 2007

Related U.S. Application Data

(60) Provisional application No. 60/765,593, filed on Feb. 6, 2006.

(51) Int. Cl.
*A23L 1/015* (2006.01)
*A23L 1/10* (2006.01)

(52) U.S. Cl. .......................... 426/622; 426/28; 426/44; 426/48; 426/455; 426/459; 426/460; 426/463; 426/464; 426/481; 426/482; 426/518; 426/618; 426/661

(58) Field of Classification Search .................. 426/28, 426/44, 48, 661, 455, 459, 460, 463, 464, 426/481, 482, 518, 618, 622
See application file for complete search history.

(56) References Cited

U.S. PATENT DOCUMENTS

| | | | | |
|---|---|---|---|---|
| 4,326,036 | A | 4/1982 | Hayes et al. | |
| 4,333,611 | A | 6/1982 | Zuker et al. | 241/1 |
| 4,414,330 | A | 11/1983 | Zucker et al. | 435/93 |
| 6,254,914 | B1 | 7/2001 | Singh et al. | 426/482 |
| 6,566,125 | B2 | 5/2003 | Johnston et al. | |
| 6,740,508 | B2 | 5/2004 | Ulrich et al. | |
| 6,835,558 | B2 | 12/2004 | Van Lengerich et al. | |
| 6,899,910 | B2 | 5/2005 | Johnston et al. | |
| 2004/0187863 | A1 | 9/2004 | Langhauser | |
| 2006/0040024 | A1 | 2/2006 | Srinivasan et al. | |
| 2006/0251764 | A1 | 11/2006 | Abbas et al. | 426/53 |

(Continued)

FOREIGN PATENT DOCUMENTS

DE 2918212 11/1980

OTHER PUBLICATIONS

Singh, N. et al. "Hydrocyclone Procedure for Starch-Protein Separation in Laboratory Wet Milling" 1995 , Cereal Chemistry, pp. 344-348.*

(Continued)

*Primary Examiner*—Helen F Pratt
(74) *Attorney, Agent, or Firm*—Patricia A. Sweeney

(57) ABSTRACT

An improved wet milling process is provided that allows for separation of seed coat particles from the horny endosperm particles of seed. The process uses soaking and grinding to produce seed coat flake particles and horny endosperm particles that may be separated using movement of liquid slurry of the particles, providing hydraulic lift to separate the seed coat particles. Improvements in the process allow for omitting addition of sulfur compounds to the process. By-products of wet milling with improved properties are provided.

29 Claims, 2 Drawing Sheets

U.S. PATENT DOCUMENTS

2006/0251791 A1 * 11/2006 Rubio et al. ................ 426/622

OTHER PUBLICATIONS

Dellweg et al. (1988) "Ethanol fermintation: suggestions for process improvements" Process Biochemistry, vol. 23: 100-104.

Singh et al. (1999) "Recovery of fiber in the corn dry-grind ethanol process: a feedstock for valuable coproducts" Cereal Chemistry 76(6):868-872.

Singh et al. (1996) "Effect of soak time, soak temperature and lactic acid on germ recovery parameters" Cereal Chemistry 73(6):715-720.

Singh et al. (2007) Process and Engineering Effects on DDGS Products—Present and Future. Proceedings on the 5th Mid-Atlantic Nutrition conference. Simmermann, N.G., ed., University of Maryland, College Park, MD. p. 82-90.

Murthy et al. (2006) Evaluation and strategies to improve fermentation characteristics of modified dry grind corn processes. Cereal Chem. 83:455-4459.

Noll et al. (2007) Formulating poultry diets with DDGS—how far can we go? Proceedings on the 5th Mid-Atlantic Nutrition conference. Zimmermann, N.G., ed., University of Maryland, College Park, MD p. 91-98.

Waldroup et al. (2007) Biofuels and Broilders—compeittors or Cooperators? Proceedings on the 5th Mid-Atlantic Nutrition conference. Zimmermann, N.G., ed., University of Maryland, College Park, MD. p. 25-34.

Srinivasan et al. (2006) Economics of Fiber Separation from Distillers Dried Grains with Solubles (DDGS) Using Sieving and Elutriation. Cereal Chem. 83(4): 324-330.

* cited by examiner

PROCESSES FOR RECOVERY AND SEPARATION OF GRAIN PERICARP FROM ENDOSPERM

REFERENCE TO RELATED APPLICATIONS

This application claims priority to previously filed application U.S. Ser. No. 60/765,593, filed Feb. 6, 2006, the contents of which are incorporated in their entirety.

BACKGROUND

Grain crops are grown for a variety of purposes, such as in feed, food and industrial applications. In producing and using grain, it is common that the different components of the grain need to be separated for optimum use in an industry. In crops in which the grain has a seed coat or pericarp, separation of the pericarp from the other seed components, the endosperm and embryo (germ), is desirable.

For example, one such application is in the separation of these seed components in the use of crop grain to produce ethanol. The replacement of fossil fuel as an energy source has led to interest in identifying renewable energy sources. One such source is the use of crop plants to produce ethanol. An example of one such crop plant is corn, used to produce ethanol, typically using either wet milling or dry grinding processes. In wet milling, corn is steeped in a liquid mixture including sulfur dioxide for a period of between 24 and 36 hours to soften the materials and loosen the components of the kernel. The corn and liquid is put in a mill that grinds the corn to free the germ from the kernel. The germ floats to the top of the slurry and can be separated. The starch, protein and fiber that remain are separated to produce pure starch. The starch is cooked and fermented, and finally distilled to produce ethanol. In dry grind ethanol production, corn is ground, mixed with water, cooked, fermented and distilled.

An important aspect of increasing the feasibility of ethanol production is to optimize use of the by-products produced in this process. High raw material and costs of bringing the raw material to plants, the cost of enzymes, yeast and chemicals used in the process, and capital and labor costs are limitations on economics of ethanol production. In the dry-grind process, no distinction is made between the fermentable starch and non-fermentable components of the seed, namely the germ, fiber and protein. These components are recovered together as a single entity, and are termed distillers dried grains with solubles, also known as DDGS. There is keen interest in the separation of these components from each other, and improvement in purity, in order that they may be sold for separate uses and improve the economics of the operation. The ability to market and sell DDGS is a limiting factor in the growth and expansion of dry-grind ethanol production facilities. Conventional wet milling provides an alternative to produce value-added products from corn, however, this process requires a large capital investment and focuses on producing clean starch for further processing into modified starches, corn syrup, high fructose corn syrup and other products.

With the increase in ethanol production from dry-grind facilities, DDGS production has doubled to 7 MM metric tons from 2000 to 2005. During this time period, the average market value of DDGS has declined from approximately $115/ton to $65/ton. This represents an annual decrease of 10% per year. The demand for renewable energy sources will continue to offset the limited availability of fossil fuels. With the continued expansion of ethanol to meet demand for energy, the trend in declining DDGS prices will likely continue.

Previous attempts have been made to separate fiber from endosperm and germ. One example is found at Singh et al., U.S. Pat. No. 6,254,914, in which a two-step process is used where specific gravity of a slurry including germ and fiber is maintained at 7.5 to 11 Baumé to remove germ, and in the second step, fiber removed by increasing the specific gravity to 11 to 16 Baumé. In an alternative, fiber and germ are removed by subjecting the slurry to a Baumé of 11 to 16.

Thus there is a need to improve recovery and purity of these components of the seed.

SUMMARY OF THE INVENTION

The process of the invention improves on wet milling conventional techniques in which seed is processed such that flakes of seed coat particles are produced that are thinner and flatter than horny endosperm particles, larger than fiber produced through conventional wet milling, and have lower density than the horny endosperm particles that are also present in the solids fractions after germ removal. The seed is soaked in liquid without the use of sulfur compounds, preferably from six to 24 hours and preferably at a temperature of 140° C. to 160° C. Germ is removed through conventional wet milling methods, followed by fiber removal which can be separated by movement of a liquid slurry of the particles resulting in hydraulic lift of the flakes. Improved by-products of wet milling are produced, which do not contain added sulfur compounds and having increased purity.

DESCRIPTION OF EMBODIMENTS OF THE INVENTION

Figure 1:
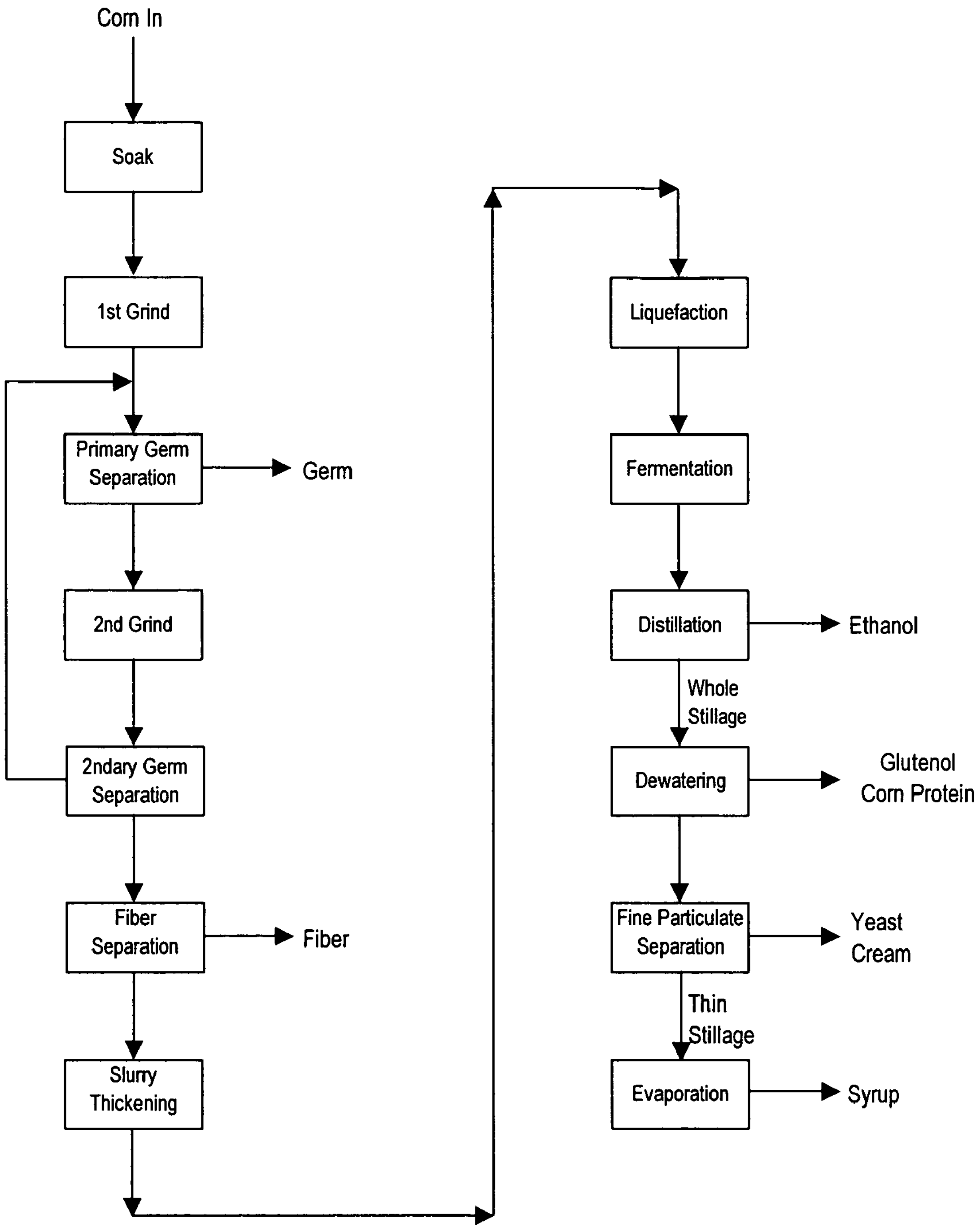
FIG. 1 shows the ethanol process with separation and recovery of grain components.

The current invention has been developed as an improved means of processing by separating the seed components, rather than producing distillers dried grains with solubles, and is particularly useful in corn dry grind processes for the fuel ethanol industry. This new process is an economical alternative to conventional wet milling, and offers several advantages over the standard dry-grind process in terms of increased revenue from co-products and reduced energy consumption. The objective of this process is to produce value-added germ, fiber and protein by-products in addition to a concentrated carbohydrate fermentation feedstock. These provide improved by-products in the process which will bring higher value to such by-products and improved feed product when fed to animals.

Grain consists of a seed coat, which is an outer layer, sometimes also referred to in the milling industry as pericarp, or bran. It is the fiber component of the grain. Endosperm is the starch and protein tissue of the grain. Endosperm further consists of the soft floury layer, and the hard layer called the horny endosperm, also referred to in the milling industry as grit. It contains more protein than the floury portion.

During the development of this process, it was discovered that the starch-gluten matrix is not completely broken down in the soaking process, as in conventional wet mill steeping, which uses sulfur dioxide or sulfurous acid. The present invention provides considerable advantage in that sulfur compounds are not used in the process, thus providing an end product which does not contain added sulfur compounds.

Plant seed may produce a modest amount of native sulfur compounds, but in this process, no non-native sulfur compounds are added. This improves palatability of the by-products in the process, and the uses to which it may be applied. What is more, the by-products, as outlined more fully below, have increased purity, and in the instance of syrup by-product, for example, have increase phosphorus, including increased available phosphorus. By available phosphorus is meant phosphorus in a food product that can be mostly absorbed by the animal consuming the product, as opposed to being excreted after digestion. In using the term by-product is meant compounds which are produced in an ethanol wet milling process, other than ethanol. Improving the quantity, purity and usefulness of these by-products is one advantage of the current process.

Several advantages are provided with the process of the invention. In this new process, the horny endosperm (grit) in the corn is not reduced to a fine particle suspension of starch and gluten. In conventional wet milling, sulfur compounds are used in the soaking step, which breaks the starch-gluten bonds in the horny endosperm to release starch and protein molecules. As a result, a significant amount of starch sticks to the fiber, giving the fiber particles a higher specific gravity. By avoiding use of sulfur compounds, one improves the resulting end by-product, but also allows the fiber particles to retain their natural difference in density, rather than having increased density due to the excess starch released clinging to the fiber particles. What is more, in conventional wet milling, horny endosperm is ground until it has the consistency of a fine powder which is suspended in liquid. Typically, a third grind reduces the horny endosperm to a liquid slurry. This fine powder may be, by way of example, about 1/16 inch in diameter and smaller. Here, instead, the horny endosperm is coarsely ground so that a large portion of the horny endosperm remains intact as relatively large pieces that are a function of the mechanical grinding steps while the floury endosperm may be dispersed into a fine suspension. The horny endosperm is coarsely ground such that among the particles are discrete visible particles that are as large as, for example 1/8 inch to 1/4 inch in diameter or more. This allows one to take advantage of the shape of the horny endosperm/grit in separation. In a further embodiment of the invention, the seed is soaked under conditions that allow the seed coat to pop off the seed in large pieces. Again, the seed coat flakes are not ground finely but rather coarsely ground, resulting in flakes that are larger than in conventional wet milling. Such flakes will be, for example, at least four times larger than those produced in conventional wet milling. This compares to conventional wet-milled fiber which is about 1/8"×1/4" and smaller. The resulting flake particles are thinner and flatter than the horny endosperm particles. The shape and size of the grit and seed coat particles in the absence of any change to their naturally occurring differences in density allows for the particles to be separated using classification. Thus, movement of the slurry allows hydraulic lift, not an application of specific gravity to the liquid, to cause the flakes to move to the top of the liquid. Hydraulic lift refers to movement of the liquid slurry which carries the flakes upward. In other words, the shape, size and density of the flakes which result from the process, which do not have an increased density as a result of excess starch clinging to the flakes due to break down of starch matrix of the endosperm, allows the natural difference in density to carry the flakes upward, rather than the application of specific gravity to provide an artificial density differentiation to the particles.

The reduction of the starch-gluten matrix in conventional wet mill steeping is the cornerstone of the process that makes fiber, starch and gluten separation possible. In conventional wet milling, once the endosperm (starch and gluten) has been fully released into suspension, the fiber is screened out using a 50-micron pressure screen that allows the starch and gluten to pass through while retaining the fiber. In the new process, the large particle size of the horny endosperm, or grit, required a different approach. It was discovered that the grit could be removed from the fiber by classification, which in one embodiment may use a device such as a hydroclone operating at various pressures and low suspended solids.

The present invention as described uses the principles of classification to separate fiber from the horny endosperm. Classification is defined as the ability of gravity or gravity enhanced separation equipment to selectively distribute insoluble solids in a fluid based on particle size, shape and density as constrained by concentration and viscosity.

The current invention can be applied to all grains with a seed coat, in which the cellulosic seed coat can be cleanly separated from a starchy endosperm in large pieces and have naturally occurring differences in density. Examples of these include corn, wheat, sorghum, rice, barley, rye, oats and amaranth.

Further, the current invention may by used to clean debris from straws, grasses and various other biomasses as the technology to convert biomass to ethanol improves and these become viable fermentation feed stocks. This is envisioned as biomass feed stock that is chopped into about 1/4" particles, slurried in liquid and processed to remove dirt, weed seed and other foreign contaminants.

First, the germ (the embryo of the seed) is separated from the endosperm and fiber. There then remains starch and protein of the endosperm and fiber of the seed coat/pericarp. In a preferred embodiment, the floury endosperm is in the form of a suspended solid in the liquid fraction of the slurry. The grit is in the shape of an angular sphere and is further separated from fiber using classification, in which the shape and particle density are used to separate it from fiber. The floury endosperm moves off in the process with the liquid fraction.

In an embodiment, the process involves soaking the seed in water, which aids in the release of the germ from the rest of the seed usually followed by coarsely grinding the seed. In a preferred embodiment, the soaking conditions are about 140° F. or more and preferably at about 150° F. to about 160° F. (or 60° C. to 71° C.) for a time period of about six to about 24 hours. Temperature above 140° F. reduces bacterial contaminants. These conditions aid in the release of the seed coat/pericarp to produce large flakes which enable the classification in the subsequent process.

The soaking conditions in a further embodiment may also include the addition of an enzyme to aid in a very clean separation of seed coat/pericarp from endosperm. Any enzyme that is effective in aiding the separation of the seed coat may be employed in the invention. In a preferred embodiment, the enzyme will be active within the temperature ranges outlined above, of 140° C. to 160° C. In a further preferred embodiment the enzyme is active within of pH of about 4 to about 8. However, one skilled in the art will appreciate that the process can be varied in temperature and pH considerably and that enzymes which may optionally be added to the process are varied. Examples of such enzymes include amylo-glucosidases which convert oligosaccharides to individual glucose molecules; proteases which break down protein structure; and cellulases. In a preferred embodiment, the enzyme is an alpha amylase enzyme. Very small amounts of enzyme can be used in this process, which is preferable since enzymes contribute to cost of the procedure. As little as about 0.0003% weight dry substance (DS) corn may be used.

In preferred embodiments, the amount of enzyme may be from about 0.006% to about 0.0172% or in another preferred embodiment about 0.0013% to about 0.0046% wt DS corn. A particular advantage of the present process is that sulfur dioxide is not needed in the soaking portion, thus eliminating sulfur contamination of the entire process and co-products.

In the grinding processes, the pericarp will be released from the endosperm in flakes. In preferred embodiments of the invention, the flake particles will be thinner, flatter and less dense than the horny endosperm particles. In an embodiment of the invention, the kernel will be ground at least once. When a first grind is used, in an embodiment of the invention, it is ground such that the endosperm does not become finely ground. Rather, a coarse grind is used as opposed to reducing the entire endosperm to a powder. One advantage of this is that the floury endosperm, because it contains less protein, will become more finely ground than the horny endosperm, which has more protein. The floury endosperm will thus be dispersed into the liquid of the slurry, where the horny endosperm will be in larger pieces. One skilled in the art appreciates that there are many variations in the grinding process that allow for these results. A first grind typically results in one to six whole kernels per one pint sample, where a second grind produces no whole or half kernels, but visible chunks of horny endosperm and pericarp. In one preferred embodiment, if passed though a Tyler 12 sieve mesh screen after the second grind, about 50% of the total endosperm would be on top of the screen; or, measured another way, about 80% of the horny endosperm would be on top of the screen. Clearly one skilled in the art will appreciate there are various means to achieve the appropriate size particles.

A slurry is formed and the germ separated from the slurry by floating the germ which may be accomplished using a device such as a hydroclone. The slurry specific gravity is controlled such that the germ floats off of the top and the fiber and endosperm sink. In preferred embodiments, the specific gravity is measured as Baumé (Be), which commonly is between 7 and 9 Be, and more preferably between 6.5-7.5 Be. The differential pressure across the hydroclone is typically controlled from 35 to 45 pounds per square inch (psi). This process of grinding and separating using specific gravity may be repeated in order to optimize separation and remove residual germ from the fiber and endosperm.

The fiber and endosperm may then be screened followed by mixing the particles with water to form a dilute slurry. Using classification, advantage is taken of the large flake shape of the fiber as released from the endosperm. These flakes are similar to sails of a sailboat in shape, while the grit is more similar in shape to a bb bead. The slurry is introduced into a device that allows for movement of the slurry to separate the pericarp such that the flake-like shape allows the pericarp fiber to rise like a kite as a result of hydraulic lift, while the endosperm grit falls. By using classification, one does not need to rely upon any particular specific gravity or Baumé applied to the slurry. The Baumé can be 0 or higher, and preferably is at least about 1 Be. Rather, hydraulic lift as a result of movement of the slurry is used to allow for separation by taking advantage of differences in settling velocities as a result of the different shapes and densities. In another embodiment, a slight centrifugal force may be applied to the slurry. If used, the centrifugal force aides in moving the grit to the outside while the fiber is carried by the hydraulic force of the water. Centrifugal force used should not be so excessive that it overcomes hydraulic force that is separating the components using different settling velocities In one embodiment, a hydroclone is used, in which a slight pressure drop is applied allowing for movement of the slurry. In a preferred embodiment, the pressure drop is a pressure that is below the pressure used in the germ separation. Preferably, it is less than about 35 psi, and more preferably, it is about 20 psi.

One skilled in the art will appreciate that a particular device to produce the movement is not required, as long as it produces the separation of the grit and fiber. The hydroclone is a static device that applies centrifugal force to a multiple phase mixture to promote the separation of relatively heavy components from the mixture. In prior applications, use of a particular range of specific gravity, typically measured in Baumé, was used in conjunction with the movement of the carrier fluid or slurry in order to separate pericarp from endosperm. Here, the specific gravity of the fluid is not critical. For example, in another embodiment, elutriation can be used for fiber removal. Elutriation uses the principles of classification in which the particles are separated using the differences in settling velocities. It will be determined, in an upflow condition, that the dilute fiber/grit slurry velocity can be reduced to allow the grits to settle to the bottom while maintaining a fluidizing velocity where the fiber is hydraulically carried with the water out the top.

The underflow will contain a concentration of endosperm grits. The fiber separation process may be repeated. The starch and grits in the slurry may be advanced to liquefaction, in which steam is applied and the starch gelatinized. In another embodiment, this step may be skipped, where enzymes are used instead, such that this step is not necessary. The starch in the slurry is converted to sugars that are consumed by the yeast during fermentation. The residual protein is recovered after fermentation.

A variety of by-products are produced which are unique by-products of dry grind ethanol production. One of the advantages of the by-products of this process is that they do not contain added sulfur compounds. Among by-products of the invention is seed germ/embryo that has at least about 42% oil and no detectable non-native sulfur compounds; seed coat/bran/fiber by-product which has less than about 8% dry substance starch, and at least about 80% dry substance neutral detergent fiber, with no non-native sulfur compounds; protein by-product having at least about 45% dry substance protein, no non-native sulfur compounds and high levels of available phosphorous; yeast cream having at least about 57% dry substance protein without added sulfur; and syrup having at least about 0.7% or more total phosphorus and at least about 50% available phosphorus.

The following is intended to be illustrative without limiting the scope of the invention.

EXAMPLE

The following references FIG. 1: Ethanol Process with Separation and Recovery of Grain Components.

Corn Soaking

The corn is soaked in 155-160° F. water for 6-24 hours. Alpha-mylase enzyme is added to the soak water at a concentration of ranging from 0.0006-0.0172% wt DS corn and preferably 0.0013-0.0046% wt DS corn. The soak water is recirculated and heated to prevent cold pockets in the soak tank. This soaking process hydrates the kernel to about 45% moisture, softens the endosperm around the germ and loosens the pericarp prior to grinding.

Grinding and Germ Separation

The initial grinding step and germ removal is very similar to the process used in conventional corn wet milling. The $1^{st}$ grind mill cleaves the kernel to free the germ from the endosperm without damage to the germ. Water is added to the corn to form a slurry. The slurry is adjusted to 7-9 Baumé and more preferably 6.5-7.5 Be suspended solids. This range of the carrying fluid takes advantage of the specific gravity differences between germ and starch slurry. The germ becomes buoyant and "floats". The germ is removed using a 4-pass counter-current hydroclone system. The 1st pass germ is removed from the process where it floats out the overflow. All subsequent passes are recycled back to the 1st pass feed tank to increase the germ concentration feeding the 1st pass hydroclone. The slurry passes through the 2nd grind mill after 2 passes of germ removal to free any residual germ from the pericarp or endosperm, then pumped through the final 2 passes of germ removal.

The pericarp is also released from the endosperm in the two grind steps. With proper soaking, the pericarp releases freely from the endosperm in large pieces. The large particle size and natural density differences makes the classification of these two fractions easier.

Fiber Separation

After the germ is removed, the horny endosperm (grit) and fiber are removed from the suspended starch slurry using a 120° pressure screen. The horny endosperm and fiber are re-slurried using process water at a ratio of 2-4:1 water to solids to decrease the amount of suspended solids. Enough dilution water is added to adjust the suspended starch solids to 5.3-8.9% (3-5 Be'), however, this may range from 0 Be, 1 Be or higher. The millstream temperature is also controlled above 145° F. to minimize the viscosity of the carrying fluid to further aid in classification.

A hydroclone is used to remove the grit from the fiber, however the principles of classification apply. The fiber is the shape of a flake, while the grit is the shape of an angular sphere. The fluidizing velocity of the flake in the carrying fluid is much lower due to the significantly larger ratio of the flake's surface area to mass as compared to the grit. As these particles enter the hydroclone, the induced centrifugal force will more significantly affect the grit, since it can move more easily through the fluid, forcing it to the outer wall and down to the underflow. In comparison to the grit, the shape of the fiber will result in the flake being more affected by hydraulic action than by centrifugal force. The fiber will consequently require more force (as more flow and higher differential pressure) to move to the outer wall. Therefore, at low differential operating pressures, the fiber will hydraulically flow with the carrying fluid through the overflow. At higher differential pressures the centrifugal force will begin to overcome the hydraulic force. The fiber will tend to follow the grit to the outer wall where it will flow with the grit out the underflow resulting in poor efficiency and recovery.

Figure 2:
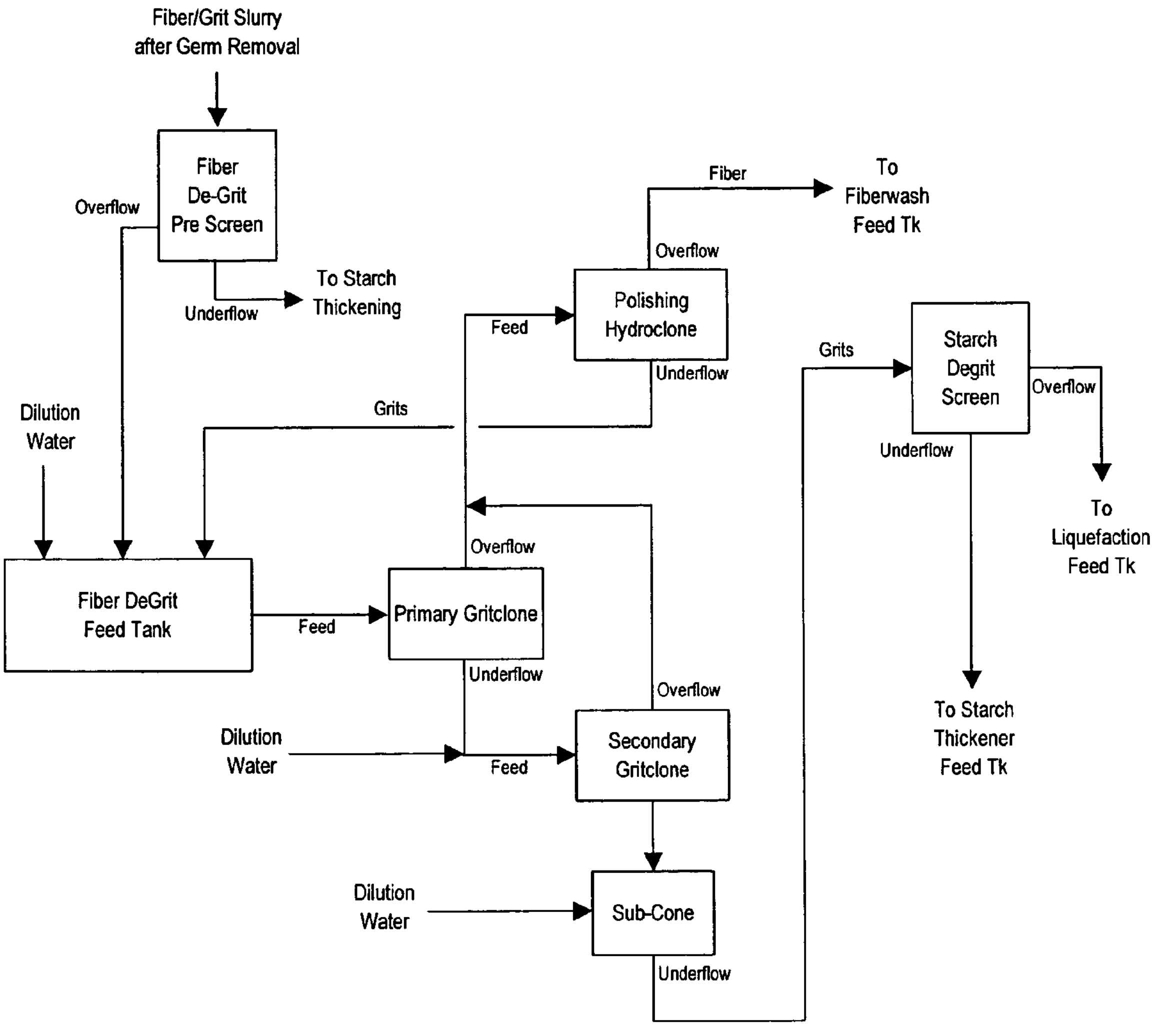
FIG. 2 shows the method developed for recovering pericarp (fiber) from corn

The fiber/grit separation hydroclones, or gritclones, are configured as a 2-pass removal system with an additional polishing stage for the fiber. See FIG. 2: Fiber/Grit Separation Process Flow Diagram for details. The fiber/grit slurry is pumped to the Primary Gritclone at a feed pressure ranging from 45-20 psig, with an optimum pressure of about 20-psig. As the slurry enters the hydroclone, the grits impinge on the outer wall and flow to the bottom where they are removed through the underflow nozzle. The underflow nozzle size is a function of the grit concentration in the slurry. The underflow nozzle size is restricted to ⅜-1¼" diameter to force the majority of the fluid out the overflow. The fluid flow hydraulically carries the fiber out the overflow. Unlike germ hydroclones, there is no restriction or pressure control on the overflow. The differential pressure between the feed and overflow is less than 35-psig, with an optimum differential pressure of around 20-psig.

The Primary Gritclone underflow is re-slurried and passed through the Secondary Gritclone, which also operates at less than 35-psig differential pressure between the feed and overflow, with an optimum differential pressure of about 20-psig The remaining fiber is removed. The Secondary Gritclones are equipped with a sub-cone to introduce additional dilution fluid and improve separation efficiency.

The overflows from the Primary and Secondary Gritclones contain about 90% fiber and about 10% fine grits. These two streams are combined and pumped to a polishing hydroclone. The function of the polishing hydroclone is to remove the remaining grits and produce a grit-free fiber stream. The polishing hydroclone can be fed at a higher pressure, 60-90 psig. The grits are removed out the underflow nozzle with some fiber and recycled back to the feed tank. The overflow from the polishing hydroclone consists of fiber in dilute starch slurry that is then washed using a series of pressure screens and counter-current water flow.

Testing of a single hydroclone successfully removed 56% DS neutral detergent fiber (NDF) from the corn slurry and resulted in a carbohydrate stream with 1.8% NDF. The system as described is expected to remove 65% DS total NDF and 90% of the pericarp from the corn slurry. This resulting carbohydrate stream is predicted to be less than 1.0% NDF.

Slurry Thickening and Liquefaction

With the germ and fiber removed, the resulting carbohydrate stream has significantly reduced viscosity. The starch can be concentrated prior to liquefaction to form a slurry ranging from 40-45% DS. This high solids slurry is then liquefied, and in an embodiment can be liquified using steam injection and a high-shear device. Any high-shear equipment can be useful, which will deliver shear on the composition sufficient to decrease viscosity of the carbohydrate composition. In an embodiment a high-shear device can be a high speed disintegration device such as a continuous colloid type mill operating on a rotor-stator principle. An example of such devices is as one referred to as a Supraton®. See for example those available at www.centrysis.com and www.centrifuge-systems.com/neu/main_supraton.htm; and descriptions by Supraton et al. at German Application DE2918212. See also U.S. Pat. No. 4,414,330; and Dellweg et al. (1988) "Ethanol fermentation: suggestions for process improvements" *Process Biochemistry,* Vol. 23: 100-104. The stream is fed through an inlet into the machine, passed through the rotor-stator system, where the shearing forces change at a high frequency, and is forced out radially. The starch slurry can be liquefied at temperatures as low as 170° F.

The carbohydrate stream is sent to fermentation and diluted with backset. The backset may be varied to produce a higher concentration of ethanol than is currently achievable in the conventional dry-grind plant. The fermented mash is distilled to remove the ethanol. The resulting high-protein whole stillage, which is low in fat and NDF, may be dewatered to produce a low sulfur, highly available phosphorous corn protein cake, marketed as Glutenol™, and thin stillage. The thin stillage contains very fine particulate yeast bodies that can be removed from the soluble solids. The solubles may be concentrated using an evaporator to produce syrup In the above example, the following by-products were produced from corn seed using the process of the invention:

Corn Germ: The germ is the high-oil fraction of the corn. The germ may be washed, dewatered and dried to produce germ that contains a minimum of 42% oil and no non-native sulfur compounds. The dried germ may be solvent extracted using non-stainless processing equipment to produce a high protein germ cake that contains about 30% DS protein, which is about 50% higher than cake from conventional wet milled germ.

Bran or Fiber: The resulting fiber may be washed with clean water in a counter-current wash system, dewatered and dried to produce a product with less than 8% DS starch, more than 80% DS NDF and no non-native sulfur compounds. This product has applications as a dietary fiber food ingredient for human and animal consumption. The concentrated syrup may also be added to this fiber to produce a higher protein bran product marketed as ProBran™ used as feed for beef cattle and dairy cows. In comparison, conventional wet-milled fiber ranges from 16-24% DS starch.

Carbohydrate: The concentrated carbohydrate stream, which also contains the corn protein, is higher in dry solids content. The higher DS slurry improves overall plant efficiency by liquefying at a lower temperature and utilizing less water in fermentation. Further energy efficiency is realized in distillation due to less water from fermentation. Fermentation is now limited by the alcohol tolerance of the yeast.

Corn Protein: The protein recovered after fermentation and distillation is low in fat and NDF, and high in available phosphorous. The Glutenol corn protein contains a minimum 45% DS protein, and about 23% DS NDF, 2.0% crude fat, no non-native sulfur compounds and over 40% non-phytate (available) phosphorous. Conventional wet-milled gluten is a minimum of 60% protein, contains added sulfur from SO2 residues and contains less than 20% phosphorous in the non-phytate form which is similar to the level found in native corn grain.

Yeast Cream: The yeast cream is high in protein, low in fat and thought to contain unidentified growth factors or pro-biotics that are beneficial to swine and chickens. The yeast cream is about 57% DS protein. The yeast cream may be flash dried and sold as a separate product, separated and added to the glutenol, or concentrated with the syrup and added to the glutenol to produce CPC. Conventional wet milled yeast cream has about 0.4% sulfur with 36-60% protein.

Syrup: The concentrated syrup may or may not contain the yeast bodies. The syrup is high in phosphorus, contains no non-native sulfur compounds and may be added to the fiber to produce ProBran or to the Glutenol to be marketed as Corn Protein Concentrate (CPC™). The syrup has about 0.7% to 1.4% total phosphorus and at least about 50% available phosphorus. Total phosphorus in corn gluten feed is about 0.9% with about 0.22% available.

All references cited are incorporated herein by reference.

What is claimed is:

1. A method of separating portions of a plant seed from one another wherein the plant seed comprises a seed coat, germ, and an endosperm comprising a floury endosperm and a horny endosperm, the method comprising:

(i) soaking a plant seed in liquid which does not contain added sulfur compounds;

(ii) grinding the seed at least once, such that the soaking and grinding produces at least four types of particles comprising (1) seed coat particles, (2) germ, (3) horny endosperm particles and(4) floury endosperm particles, wherein (a) the seed coat particles comprise flakes that are greater than ⅛ inch in size and are thinner and flatter in shape than the horny endosperm particles;

(b) the horny endosperm particles are greater than ⅛ inch in diameter and the production of horny endosperm particles does not release starch such that density of the seed coat flakes is increased;

(iii) producing a liquid slurry of the seed coat, horny endosperm and floury endosperm particles in which specific gravity of the seed coat flakes is lower than the specific gravity of the slurry as a result of density of the flakes not being increased;

(iv) causing movement of the slurry to produce hydraulic lift such that the seed coat particle flakes rise in the slurry as a result of movement of the liquid and the lower specific gravity of the seed coat flakes and the horny endosperm particles sink downward or outward in the slurry; and (v) separating the seed coat particle flakes from the horny endosperm particles.

2. The method of claim 1 further comprising soaking and grinding the seed such that the floury endosperm particles are ground more finely than the horny endosperm particles and are dispersed in the slurry.

3. The method of claim 1 further comprising separating germ of the seed from the seed coat and endosperm.

4. The method of claim 1 wherein the seed is soaked in water at temperature of from about 140° F. to about 160° F.

5. The method of claim 1 wherein the seed is soaked in water for about six to about 24 hours.

6. The method of claim 1 further comprising adding an enzyme to the liquid used in soaking the seed.

7. The method of claim 6 wherein the enzyme is alpha amylase.

8. The method of claim 7 wherein the enzyme is added to at least about 0.003% weight dry substance seed.

9. The method of claim 8 wherein the enzyme is added to about 0.006% to about 0.0172% weight dry substance seed.

10. The method of claim 9 wherein the enzyme is added to about 0.013% to about 0.0046% weight dry substance seed.

11. The method of claim 1 wherein the seed coat particles and horny endosperm particles are coarsely ground.

12. The method of claim 1 wherein the seed is soaked until it has a moisture content of about 45%.

13. The method of claim 1 wherein movement of the slurry is produced by a hydrocyclone.

14. The method of claim 13 wherein the separation of seed coat particles and horny endosperm particles occurs at a Baumé of less than 11.

15. The method of claim 3 further comprising separating the germ from the particles at a first pressure, prior to separating the seed coat particles from horny endosperm particles at a second lower pressure.

16. The method of claim 15 wherein the second pressure is at least about 20 psi.

17. The method of claim 1 wherein the seed is corn seed.

18. The method of claim 13, wherein wherein the separation of seed coat flakes and horny endosperm particles occurs at a Baumé of 10.5 or less.

19. The method of claim 13, wherein the separation of seed coat flakes and horny endosperm particles occurs at a Baumé of 10 or less.

20. The method of claim 13, wherein the separation of seed coat flakes and horny endosperm particles occurs at a Baumé of 9 or less.

21. The method of claim 13, wherein the separation of seed coat flakes and horny endosperm particles occurs at a Baumé of 8 or less.

22. The method of claim 3 further comprising separating the germ from the particles at a first pressure, prior to separating the seed coat flakes from horny endosperm particles at the same pressure.

23. The method of claim 3, wherein the separation of seed coat flakes from horny endosperm particles occurs at the Baumé that is the same as the Baumé used to separate the germ.

24. The method of claim 3, wherein the separation of seed coat flakes from horny endosperm particles occurs at a lower Baumé than is used to separate the germ.

25. A method of separating portions of a plant seed from one another wherein the plant seed comprises a seed coat, germ, and an endosperm comprising a floury endosperm and a horny endosperm, the method comprising:

(i) soaking a plant seed in liquid which does not contain added sulfur compounds;

(ii) grinding the seed at least once, such that the soaking and grinding produces at least four types of particles comprising (1) seed coat particles, (2) germ, (3) horny endosperm particles and(4) floury endosperm particles, wherein (a) the seed coat particles comprise flakes that are thinner and flatter in shape than the horny endosperm particles, (b) the horny endosperm particles are coarsely ground and the production of horny endosperm particles does not release starch such that density of the seed coat flakes is increased;

(iii) producing a liquid slurry of the seed coat flakes, horny endosperm particles, and floury endosperm particles in which specific gravity of said seed coat flakes is less than the specific gravity of the slurry;

(iv) causing movement of the slurry with a hydrocyclone wherein separation of seed coat flakes and horny endosperm particles occurs at a Baumé of 10.5 or less; and (v) separating the seed coat flakes from the horny endosperm particles.

26. The method of claim 25 wherein said Baumé is 10 or less.

27. The method of claim 25, wherein said Baumé is 9 or less.

28. The method of claim 25 wherein said Baumé is 8 or less.

29. A method of separating portions of a plant seed from one another wherein the plant seed comprises a seed coat, germ, and an endosperm comprising a floury endosperm and a horny endosperm, the method comprising:

(i) soaking a plant seed in liquid which does not contain added sulfur compounds;

(ii) grinding the seed at least once, such that the soaking and grinding produces at least four types of particles comprising (1) seed coat particles, (2) germ, (3) horny endosperm particles and (4) floury endosperm particles, wherein (a) the seed coat particles comprise flakes that are thinner and flatter in shape than the horny endosperm particles, (b) the horny endosperm particles are coarsely ground and the production of horny endosperm particles does not release starch such that density of the seed coat flakes is increased;

(iii) producing a liquid slurry of the germ, seed coat flakes, horny endosperm particles and floury endosperm particles in which specific gravity of the seed coat flakes is less than the specific gravity of the slurry;

(iv) separating germ of the seed from the seed coat flakes and endosperm at a first pressure;

(v) separating the seed coat flakes and horny endosperm particles at a second pressure which is the same or less than the first pressure.

* * * * *